United States Patent [19]

Weinberg

[11] Patent Number: 5,856,248
[45] Date of Patent: Jan. 5, 1999

[54] MICROBISTATIC AND DEODORIZING CELLULOSE FIBERS

[76] Inventor: Amotz Weinberg, 18 Nathan Hechacham St., Tel-Aviv, Israel, 63413

[21] Appl. No.: 635,549

[22] Filed: Apr. 22, 1996

[30] Foreign Application Priority Data

Apr. 28, 1995 [IL] Israel ......................... 113534

[51] Int. Cl.$^6$ ......................................... A61F 13/15
[52] U.S. Cl. ......................... 442/118; 8/116.1; 8/120; 442/228; 442/316; 442/376; 604/360; 604/375
[58] Field of Search ....................... 442/118, 228, 442/316, 376; 8/116.1, 120; 604/360, 375

[56] References Cited

U.S. PATENT DOCUMENTS

| | | | |
|---|---|---|---|
| 4,372,309 | 2/1983 | Fowler | 128/284 |
| 4,637,820 | 1/1987 | Marini et al. | 8/129 |
| 4,675,014 | 6/1987 | Sustmann et al. | 604/375 |

*Primary Examiner*—James J. Bell
*Attorney, Agent, or Firm*—Edwin D. Schindler

[57] ABSTRACT

Cellulose fibers and products comprising such fibers treated to absorb body secretions and to substantially decrease microbial growth, said fibers being chemically treated with a water soluble salt of a transition metal and an alkali and after this with a solution of a bisbiguanide compound, forming a bond between the fibers, the transition metal and the bisbiguanide. Preferred are water-soluble cupric salts as a suitable hydroxide. A preferred bisbiguanide is chlorhexidine. The products can be yarns, knitted, woven, non-woven fabrics, paper gauze and especially bandages, wound dressings, pads, diapers, sanitary napkins, tampons, bed sheets, pants, garments, towels, socks, shoe linings and underwear. Preferably between 0.1 to 3.0 weight per cent copper calculated on the cellulose is bonded to the cellulose.

8 Claims, No Drawings

MICROBISTATIC AND DEODORIZING CELLULOSE FIBERS

BACKGROUND OF THE INVENTION

When articles are applied to absorb bodily liquids discharged, bacterial decomposition of the secretion occurs and evolves the emission of unpleasant odors. In many cases such discharge due to injury leads to the growth of pathogenic microbes.

Urinary incontinence is manifested by the inability to control urination, some or all the time. It is usually caused by an underlying illness or ailment, such as paralysis or relaxation of sphincters or contraction of longitudinal muscular layer of bladder. Elderly people are more vulnerable to incontinence than younger people since their muscles and ligaments that control urination are less effective.

Urine consists of approx. 95% water and 5% solids. The main organic substances in the urine of healthy person are; urea, uric acid, creatine, creatinine and ammnonia. The inorganic substances are; sodium chloride, potassium chloride, calcium, magnesium and phosphorous compounds. In addition to the above, many other substances may be present depending on the diet and state of health of the individual. Among component substances indicating pathological states are albumin, glucose, ketone bodies, blood, pus, casts and bacteria.

The odor of freshly discharged urine of a healthy person is faintly aromatic. When urine is allowed to decompose, it emits usually a strong and offensive odor of ammoniacal nature.

People with urinary incontinence often withdraw socially. Although pads and diapers are available commercially to maintain daily hygiene, infrequent changes of them cause the decomposition of the urine. The process of decomposition of urine in the absorbing layer of the pad is accelerated due to the warming effect of the body of the user.

Menstrual flow consists of blood, vaginal and cervical secretions and tissue sloughed from the lining of the uterus. The menstrual fluid which contains microorganisms can generate malodorous volatile byproducts, over a period of as short as four hours. With some compounds in this fluid the odor can be formed as soon as it exits the body.

Excessive or prolonged perspiration of the body, may turn to be malodorous. The fetid odor is caused by decomposition of the sweat and cellular debris of the skin by bacteria and yeast.

Various compounds and products are useful in controlling malodor due to bodily fluids. Certain types are more effective against specific types of malodors.

Canadian Patent No. 474,818 discloses a sanitary napkin which incorporates a quaternary ammonium salt into the cellulose pad. The ammonium salt reacts with the odor producing matter in the liquid body excretion and prevents the subsequent development of odors.

U.S. Pat. No. 3,794,034 discloses a body waste fluid absorbent pad. A substantial portion of the pad has a water soluble, weakly acidic, buffered solid composition. The controlled pH of the buffered pad inhibits the formation of ammonia and volatile amines from the urea, uric acid, amino acid and peptones in the body waste liquid, by bacterial and enzyme action.

U.S. Pat. No. 4,372,309 discloses moisture absorbent pad incorporating bacterial static agents for the prevention of biological degradation of urine. The absorbent may also include an acidic substance (such as boric or citric acid) for absorbing volatile nitrogenous compounds.

European Patent No. 0 510 619 A1 discloses article for absorbing bodily fluids and controlling malodor created by the presence of bodily fluids. The article comprising of layers of materials; one of them may contain bacterial growth inhibitors and another may contain an odor control complex. The bacterial growth inhibitors such as solution of chlorhexidine digluconate is applied onto a carrier layer such as cotton fabric pulp and others by impregnation or spraying.

U.S. Pat. Nos. 4,637,820 and 4,675,014 disclose methods of treating cellulose materials through substituting the cellulose anhydroglucose units by anionic moieties such as: $-PO_3H^{(-)}$; $-(CH_2)_nPO_3H^{(-)}$; $-(CH_2)_nSO_3^{(-)}$; or $-(CH_2)_nCOO^{(-)}$ where n from 1 to 3; and capped by copper cations to the extent that the treated cellulose fibers bind from 0.1 to about 3% by weight of copper. The copper-modified cellulose fibrous material is claimed to possess deodorizing and microbistatic properties.

While the documents discussed above may disclose products which exhibit some of the characteristics of the present invention, none of them discloses or suggests the present invention which achieves simultaneously the following objectives:

- producing cellulose substrates (pulp, fiber-mass, yarn, fabric, non-woven, etc.) treated with bacteria growth inhibitor which can be used entirely or partly in products such as pads, diapers, sanitary napkins, bed sheets, pants, garments etc. The absorbency of the cellulose substrate is not impaired by the treatment with the bacteria growth inhibitor
- the bacteria growth inhibitor is capable of inhibiting the growth of bacteria present in bodily fluids such as urine, menstrual fluid, perspiration etc. and in the product itself while not disturbing the normal flora present on the skin's surface
- the bacteria growth inhibitor is ionic compounded to the substrate
- the activity of the bacteria growth inhibitor can be regulated
- the bacteria growth inhibitor resists purging action by a stream of bodily liquids hence it maintains its activity throughout the treated substrate under flow of liquids.
- the bacteria growth inhibitor resists washing hence it is suitable to be used, to a certain extent, also for non-disposable products.

SUMMARY OF THE INVENTION

The present invention relates to cellulose fibers and products comprising cellulose fibers treated to absorb body secretions while substantially decreasing microbial growth, said cellulose fibers being chemically modified by treatment with a water soluble salt of a transition metal and an alkali and in another step with a solution of a bisbiguanide compound, forming a bond between the fibers, the transition metal and the bisbiguanide compound. Preferably the transition metal is copper, used in a form of a water-soluble cupric salt, and the alkali is a suitable hydroxide.

A preferred bisbiguanide is chlorhexidine.

The cellulose fibers and products may be in the form of fibers, yarns, knitted woven or non-woven fabrics, paper gauze and the like. The products may be, for example, bandages, wound dressing, pads, diapers, sanitary napkins, tampons, bed sheets, pants, garments, towels, socks, shoe linings and underwear.

The present invention claims a method of preventing bacterial and enzymatic decomposition of bodily secretions and providing microbistatic properties to cellulose fibers (cotton, viscose and alike). Such fibers in loose form or as fabrics are the most common absorbent substrate for hygienic and wound dressing products.

The said method comprises of two consecutive stages. In the first stage the cellulose fibers are treated with a salt of transition metal, preferable copper. The process comprises of treating cellulose fibers in one bath containing solution of basic reagent such as NaOH (20 to 50 gram per liter solution) and cupric salt such as $CuSO_4$ then rinsing the treated fibers with water to nearly neutral pH. Alternatively, a two baths process can be applied in the first stage where in the first bath the cellulose fibers are treated with solution of cupric salt ($CuSO_4$) and in the second with solution of a basic reagent (NaOH) then rinsing with water to a nearly neutral pH. Another alternative is to use the two baths process in a reverse sequence; first the basic bath then the cupric salt bath. The first stage process yields copper cations attached to the cellulose by ionic bonds. The amount of copper bound to the cellulose fibers varies from 0.1% to 3.0% by weight.

The color of the copper treated cellulose is light blue, it inhibits growth of bacteria specifically of the anaerobic type. It was found that cellulose fibers treated by cupric salt inhibits the growth of bacterial urease, which breaks down urinary urea to ammonia. In addition, the copper compound helps to absorb any ammonia that does evolve.

The second stage of the process according to this method comprises treating the cupric derivative of cellulose in a solution of the second antimicrobial agent from the group of bisbiguanides, preferable Chlorhexidine.

Chlorhexidine is a potent antiseptic agent. It inhibits the growth of a broad spectrum of bacteria and of some lipophillic viruses (e.g. herpes and HIV) and has low mammalian toxicity. This material is available commercially as aqueous solution of chlorhexidine digluconate (20% w/v).

If the concentration of chlorhexidine in the second stage treatment bath yields an equimolar ratio between the cupric ions in the cellulose and the chlorhexidine, all the chlorhexidine is attached to the cellulose by ionic bonds. If, however, the concentrarion of chlorhexidine in the second stage treatment bath yields higher molar ratio of chlorhexidine, some of it would remain unbounded to the cellulose fibers. The color of the fibers treated by the processes of the two stages is light pink-lilac. Excessive chlorhexidine would not react with the treated cellulose. It is to be assumed that the chlorhexidine is bound to the bi-valent copper by a coordinative bonds. The complex cellulose-copper-chlorhexidine is stable to water at neutral pH and to dilute solutions of nonionic detergents at room temperature. When exposed to slight acidic or basic solutions, the chlorhexidine and some copper cations are leached out from the cellulose and act as efficient microbistatic agents.

The following examples illustrate some aspects of the present invention but are not to be constructed as limiting.

Examples 1–4 illustrate the production of deodorizing and microbistatic cellulose knitted fabric. Examples 5–9 illustrates the production of deodorizing and microbistatic loose cellulose fibers. Examples 10–11 demonstrate testing for urine odor prevention and the prevention of bacterial growth.

EXAMPLE 1

1 kg of bleached knitted cotton fabric was treated in 10 liter solution containing 500 g NaOH and 28 g $CuSO_4.5H_2O$ for 30 minutes at temperature of 25° C. The fabric was then washed under running water until the pH of the washing water was nearly 7. It was then wringed out and dried at 45° C. The color of the dried fabric was blue and its copper content was 0.6% of fabric weight.

The fabric was then immersed for 10 minutes, at 25° C. in 15 liter solution containing 431 g of 20% w/v solution of chlorhexidine digluconate. The temperature was raised at a rate of 5° C. per minute up to 75° C. and was maintained at this temperature for 20 minutes. The fabric was then wringed out and dried at 75° C. The color of the treated fabric was lilac and the content of its chlorhexidine was 0.58% of fabric weight.

EXAMPLE 2

1 kg of bleached knitted cotton fabric was treated in 3.5 liter solution containing 52.5 g $CuSO_4.5H_2O$ for 30 minutes at temperature of 25° C. Then it was transferred to another bath of 5 liter solution containing 250 g NaOH at 25° C. for 40 minutes. The fabric was then washed under running water until the pH of the washing water was nearly 7. It was then wringed out and dried at 45° C. The color of the dried fabric was light blue and its copper content was 0.53% of fabric weight. The fabric was then immersed for 10 minutes in 15 liter solution at 25° C. containing 367 g of 20% w/v solution of chlorhexidine digluconate. The temperature was raised at a rate of 5° C. per minute up to 75° C. and was maintained at this temperature for 20 minutes. The fabric was then wringed out and dried at 75° C. The color of the treated fabric was lilac and the content of its chlorhexidine was 0.51% of fabric weight.

EXAMPLE 3

1 kg of bleached knitted cotton fabric was treated in 7 liter solution containing 280 g NaOH for 40 minutes at temperature of 25° C. Then it was transferred to another bath of 5 liter solution containing 40 g $CuSO_4.5H_2O$ at 25° C. for 45 minutes. The fabric was then washed under running water until the pH of the washing water was nearly 7. It was then wringed out and dried at 45° C. The color of the dried fabric was blue and its copper content was 0.71% of fabric weight. The fabric was then immersed in 15 liter solution at 25° C. containing 485 g of 20% w/v solution of chlorhexidine digluconate. The temperature was raised at a rate of 5° C. per minute up to 75° C. and was maintained at this temperature for 30 minutes. The fabric was then wringed out and dried at 75° C. The color of the treated fabric was lilac and the content of its chlorhexidine was 0.64% of fabric weight.

EXAMPLE 4

1 kg of bleached knitted cotton fabric was treated in 7 liter solution containing 420 g NaOH for 40 minutes at temperature of 25° C. Then it was transferred to another bath of 5 liter solution containing 108 g $CuSO_4.5H_2O$ at 25° C. for 60 minutes. The fabric was then washed under running water until the pH of the washing water was nearly 7. It was then wringed out and dried at 45° C. The color of the dried fabric was blue and its copper content was 1.41% of fabric weight. The fabric was then immersed in 10 liter solution at 25° C. containing 1050 g of 20% w/v solution of chlorhexidine digluconate. After 10 minutes at 25° C., the temperature of the solution was raised at a rate of 5° C. per minute up to 75° C. and was maintained at this temperature for 30 minutes. The treated fabric was wringed out and dried at 75° C., its color was lilac and the content of its chlorhexidine was 1.18% of fabric weight.

EXAMPLE 5

1 kg of staple viscose fibers was treated in 7 liter solution containing 350 g NaOH for 40 minutes at temperature of 25°

C. Then it was transferred to another bath of 5 liter solution containing 85 g $CuSO_4 \cdot 5H_2O$ at 25° C. for 40 minutes. The fibers were then washed under running water until the pH of the washing water was nearly 7. They were then wringed out and dried at 45° C. The color of the dried fabric was blue and its copper content was 1.32% of fibers weight. The fibers were then immersed in 15 liter solution at 25° C. containing 950 g of 20% w/v solution of chlorhexidine digluconate. After 10 minutes at 25° C., the temperature of the solution was raised at a rate of 2° C. per minute up to 75° C. and was maintained at this temperature for 20 minutes. The fabric was then wringed out and dried at 75° C. The color of the treated fabric was lilac and the content of its chlorhexidine was 1.17% of fibers weight.

EXAMPLE 6

1 kg of staple viscose fibers was treated in 5 liter solution containing 20 g $CuSO_4 \cdot 5H_2O$ for 30 minutes at temperature of 25° C. Then it was transferred to another bath of 7 liter solution containing 280 g NaOH at 25° C. for 60 minutes. The fibers were then washed under running water until the pH of the washing water was nearly 7. They were then wringed out and dried at 45° C. The color of the dried fabric was light blue and its copper content was 0.28% of fibers weight. The fibers were then immersed for 10 minutes in 20 liter solution at 50° C. containing 205 g of 20% w/v solution of chlorhexidine digluconate. The treated fibers were wringed out and dried at 70° C., there color was lilac and the content of its chlorhexidine was 0.27% of fibers weight.

EXAMPLE 7

1 kg of loose bleached cotton fibers was treated in 10 liter solution containing 400 g NaOH for 40 minutes at temperature of 25° C. Then it was transferred to another bath of 5 liter solution containing 16 g $CuSO_4 \cdot 5H_2O$ at 25° C. for 60 minutes. The fibers were then washed under running water until the pH of the washing water was nearly 7. They were then wringed out and dried at 45° C. The color of the dried fabric was light blue and its copper content was 0.25% of fibers weight. The fibers were then immersed for 10 minutes in 15 liter solution at 25° C. containing 190 g of 20% w/v solution of chlorhexidine digluconate. The solution was heated to 60° C. and maintained at this temperature for 20 minutes. The treated fibers were wringed out and dried at 75° C., there color was lilac and the content of its chlorhexidine was 0.24% of fibers weight.

EXAMPLE 8

1 kg of staple viscose fibers was treated in 10 liter solution containing 300 g NaOH for 35 minutes at temperature of 25° C. Then it was transferred to another bath of 7 liter solution containing 20 g $CuSO_4 \cdot 5H_2O$ at 25° C. for 40 minutes. The fibers were then washed under running water until the pH of the washing water was nearly 7. They were then wringed out and dried at 45° C. The color of the dried fibers was blue and there copper content was 0.43% of fibers weight. The fibers were then immersed in 15 liter solution 50° C. containing 300 g of 20% w/v solution of chlorhexidine digluconate, for 40 minutes. The color of the treated fibers was lilac and the content of its chlorhexidine was 0.41% of fibers weight.

EXAMPLE 9

1 kg of loose bleached cotton fibers was treated in 10 liter solution containing 400 g NaOH for 40 minutes at temperature of 25° C. Then it was transferred to another bath of 5 liter solution containing 10 g $CuCl_2$ at 25° C. for 60 minutes. The fibers were then washed under running water until the pH of the washing water was nearly 7. They were then wringed out and dried at 45° C. The color of the dried fabric was light blue and its copper content was 0.25% of fibers weight. The fibers were then immersed in 15 liter solution at 50° C. containing 190 g of 20% w/v solution of chlorhexidine digluconate, for 40 minutes. The treated fibers were wringed out and dried at 70° C., there color was lilac and the content of its chliorhexidine was 0.23% of fibers weight.

EXAMPLE 10

Quantities of 10 ml of culture broth were added to samples of 1 gram of bleached cotton knitted fabrics. Some of the cotton samples were treated first according to Example 1. The samples were then inoculated with a suspension of each test organism. The following organisms were tested:

Staphylococcus aureus (Gram-positive coccus)

*Eschercihia coli* (Gram-negative bacillus)

*Pseudomonas aeruginosa* (Gram-negative bacillus)

*Candida albicans* (Yeast)

After incubation at 37° C. (Yeast at 30° C.) for 24 hours, The samples were examined for distinct growth.

In the case of non-treated samples, growth occurred with each strain tested, whereas in non of the treated samples could growth be detected.

EXAMPLE 11

Samples of bleached knitted cotton fabric were saturated with fresh urine of healthy males and females. Some of the samples were treated first according to Examples 1, 2 and 3. The samples were placed in polythene bags and incubated at 30° C. for 20 hours.

In the case of non-treated samples, distinct odor of ammoniacal nature could be detected, whereas in treated samples no emission of unpleasant odor has been detected.

I claim:

1. Cellulose fibers and products comprising cellulose fibers treated to absorb body secretions while substantially decreasing microbial growth, said cellulose fibers being chemically modified in a two-stage process comprising a first stage treatment with a water soluble salt of a transition metal and an alkali and a second stage treatment with a solution of a bisbiguanide compound, thereby forming a bond between the cellulose fibers, the transition metal and the bisbiguanide compound.

2. Cellulose fibers and products according to claim 1, where the transition metal is copper, used in the form of water-soluble cupric salt, and where the alkali is hydroxide.

3. Cellulose fibers and products according to claim 1, where the bisbiguanide is chlorhexidine.

4. Cellulose fibers and products according to claim 1, in the form of fibers, yarns, knitted, woven or non-woven fabrics or paper gauze.

5. Cellulose fibers and products according to claim 1 in the form of bandages, wound dressing, pads, diapers, sanitary napkins, tampons, bed sheets, pants, garments, towels, socks, shoe linings, underwear.

6. Cellulose fibers and products according to claim 3, where the molar ratio of copper salt to chlorhexidine is about 1.

7. Cellulose fibers and products according to claim 2, where the quantity of copper bound to the cellulose is between 0.1 to 3.0 weight per cent calculated on the cellulose and the quantity of chlorhexidine bound to the cellulose is between 0.1 to 1.0 weight per cent which are chemically bonded to the cellulose.

8. A product produced entirely or partially from chemically modified cellulose obtained by a process for treating cellulose fibers and a product made, at least, partially from said cellulose fibers, resulting in a substantial decrease of microbial growth when exposed to body secretions, said process comprising the steps in the order of:

treating cellulose fibers with an aqueous solution of a transition metal salt and with an alkaline solution, thereby yielding treated cellulose fibers;

rinsing said treated cellulose fibers to a neutral pH; and, treating said treated cellulose fibers with a bisbiguanide compound for forming a cellulose-transition metal-bisbiguanide bond.

* * * * *